| United States Patent [19] | [11] Patent Number: 4,606,841 |
| Basu et al. | [45] Date of Patent: Aug. 19, 1986 |

[54] AZEOTROPE-LIKE COMPOSITIONS OF TRICHLOROTRIFLUOROETHANE, ETHANOL, ACETONE, NITROMETHANE AND HEXANE

[75] Inventors: Rajat S. Basu, Williamsville; Earl A. E. Lund, West Seneca; Hang T. Pham, North Tonawanda; David P. Wilson, Williamsville, all of N.Y.

[73] Assignee: Allied Corporation, Morris Township, Morris County, N.J.

[21] Appl. No.: 675,682

[22] Filed: Nov. 28, 1984

[51] Int. Cl.⁴ .................. C11D 7/50; C23G 5/036
[52] U.S. Cl. .................... 252/171; 134/2; 134/31; 252/67; 252/153; 252/162; 252/172; 252/364
[58] Field of Search ............. 252/67, 153, 162, 171, 252/172, 364; 134/2, 31

[56] References Cited

U.S. PATENT DOCUMENTS

| 2,999,815 | 9/1961 | Eiseman, Jr. ............ 252/171 |
| 3,573,213 | 3/1971 | Burt ...................... 252/172 |
| 3,728,268 | 4/1973 | Burt ...................... 252/170 |
| 3,789,006 | 1/1974 | McMillan et al. ........ 252/171 |
| 3,881,949 | 5/1975 | Brock .................... 134/31 |
| 3,903,009 | 9/1975 | Bauer et al. ............ 252/171 |
| 4,045,366 | 8/1977 | Figiel ................... 252/171 |
| 4,279,664 | 7/1981 | Figiel ................... 134/38 |

FOREIGN PATENT DOCUMENTS 2066740B  6/1983  United Kingdom .

OTHER PUBLICATIONS

English Abstracts of Japanese Patent Nos. 81-34,798, 81-34,799, and 81-109,298.

*Primary Examiner*—Paul Lieberman
*Assistant Examiner*—Robert A. Wax
*Attorney, Agent, or Firm*—Jay P. Friedenson

[57] ABSTRACT

Azeotrope-like compositions comprising of trichlorotrifluoroethane, ethanol, acetone, nitromethane and hexane are stable and have utility as degreasing agents and as solvents in a variety of industrial cleaning applications.

16 Claims, No Drawings

AZEOTROPE-LIKE COMPOSITIONS OF TRICHLOROTRIFLUOROETHANE, ETHANOL, ACETONE, NITROMETHANE AND HEXANE

FIELD OF THE INVENTION

This invention relates to azeotrope-like mixtures of trichlorotrifluoroethane, ethanol, acetone, nitromethane and hexane. These mixtures are useful in a variety of vapor degreasing or solvent cleaning applications including defluxing.

BACKGROUND OF THE INVENTION

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room-temperature object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

For difficult to remove soils where elevated temperature is necessary to improve the cleaning action of the solvent, or for large volume assembly line operations where the cleaning of metal parts and assemblies must be done efficiently and quickly, the conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. In addition, the part can also be sprayed with distilled solvent before final rinsing.

Vapor degreasers suitable in the above-described operations are well known in the art. For example, Sherliker et al. in U.S. Pat. No. 3,085,918 disclose such suitable vapor degreasers comprising a boiling sump, a clean sump, a water separator, and other ancillary equipment.

Fluorocarbon solvents, such as trichlorotrifluoroethane, have attained widespread use in recent years as effective, nontoxic, and nonflammable agents useful in degreasing applications. Trichlorotrifluoroethane in particular has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like. For certain solvent purposes, however, trichlorotrifluoroethane alone may have insufficient solvent power. Since trichlorotrifluoroethane is non-polar, it does not remove polar contaminants well. Thus, to overcome this deficiency, trichlorotrifluoroethane has been mixed with polar components such as aliphatic alcohols or chlorocarbons such as methylene chloride. As example, U.S. Pat. No. 3,881,949 discloses the use of mixtures of 1,1,2-trichloro-1,2,2-trifluoroethane and ethanol as solvents for vapor degreasers.

The art has looked, in particular, towards azeotropic compositions including the desired fluorocarbon components, such as trichlorotrifluoroethane, which include components which contribute additionally desired characteristics, such as polar functionality, increased solvency power, and stabilizers. Azeotropic compositions are desired because they exhibit a minimum boiling point and do not fractionate upon boiling. This is desirable because in the previously described vapor degreasing equipment with which these solvents are employed, redistilled material is generated for final rinse-cleaning. Thus, the vapor degreasing system acts as a still. Unless the solvent composition exhibits a constant boiling point, i.e., is an azeotrope or is azeotrope-like, fractionation will occur and undesirable solvent distribution may act to upset the cleaning and safety of processing. Preferential evaporation of the more volatile components of the solvent mixtures, which would be the case if they were not azeotrope or azeotrope-like, would result in mixtures with changed compositions which may have less desirable properties, such as lower solvency towards soils, less inertness towards metal, plastic or elastomer components, and increased flammability and toxicity.

A number of trichlorotrifluoroethane based azeotrope compositions have been discovered which have been tested and in some cases employed as solvents for miscellaneous vapor degreasing applications. For example, U.S. Pat. No. 2,999,815 discloses the azeotrope of 1,1,2-trichloro-1,2,2-trifluoroethane and acetone; U.S. Pat. No. 3,573,213 discloses the azeotrope of 1,1,2-trichloro-1,2,2-trifluoroethane and nitromethane; U.S. Pat. No. 4,045,366 discloses ternary azeotropic-like mixtures which contain 1,1,2-trichlorotrifluoroethane, nitromethane and acetone; U.S. Pat. No. 3,903,009 discloses the ternary azeotrope of 1,1,2-trichloro-1,2,2-trifluoroethane, nitromethane and ethanol; U.S. Pat. No. 3,789,006 discloses the ternary azeotrope of 1,1,2-trichloro-1,2,2-trifluoroethane, nitromethane and isopropanol; U.S. Pat. No. 3,728,268 discloses the ternary azeotrope of 1,1,2-trichloro-1,2,2-trifluoroethane, acetone and ethanol; U.S. Pat. No. 4,279,664 discloses an azeotrope-like composition consisting of trichlorotrifluoroethane, acetone and hexane; U.K. Pat. No. 2,066,840B discloses azeotrope-like mixtures of 1,1,2-trichloro-1,2,2-trifluoroethane, ethanol, nitromethane and acetone; Japanese Pat. Nos. 81-34,799 and 81-34,798 disclose azeotrope-like mixtures of 1,1,2-trichloro-1,2,2-trifluoroethane, ethanol, nitromethane and 3-methylpentane or 2,2-dimethylbutane or 2,3-dimethylbutane and Japanese Pat. No. 81,109,298 discloses azeotrope-like mixtures of 1,1,2-trichloro-1,2,2-trifluoroethane, ethanol, n-hexane and nitromethane.

The art is continually seeking new fluorocarbon based azeotropic mixtures or azeotrope-like mixtures which offer alternatives for new and special applications for vapor degreasing and other cleaning applications.

It is accordingly an object of this invention to provide novel azeotrope-like compositions based on 1,1,2-trichloro-1,2,2-trifluoroethane which have good solvency power and other desirable properties for vapor degreasing and other solvent cleaning applications.

Another object of the invention is to provide novel constant boiling or essentially constant boiling solvents which are liquid at room temperature, will not fractionate under conditions of use and also have the foregoing advantages.

A further object is to provide azeotrope-like compositions which are relatively nontoxic and nonflammable both in the liquid phase and the vapor phase.

These and other objects and features of the invention will become more evident from the description which follows.

DESCRIPTION OF THE INVENTION

In accordance with the invention, novel azeotrope-like compositions have been discovered comprising trichlorotrifluoroethane, ethanol, acetone, nitromethane and hexane, with 1,1,2-trichloro-1,2,2-trifluoroethane being the trichlorotrifluoroethane of choice. In a preferred embodiment of the invention, the azeotrope-like compositions comprise from about 67.6 to about 90.5 weight percent of 1,1,2-trichloro-1,2,2-trifluoroethane, from about 1.5 to about 8.1 weight percent of ethanol, from about 7.4 to about 16.6 weight percent of acetone, from about 0.05 to about 0.5 weight percent of nitromethane and from about 0.2 to about 8.3 weight percent of hexane. In another preferred embodiment of the invention, the azeotrope-like compositions comprise from about 79.6 to about 89.9 weight percent of 1,1,2-trichloro-1,2,2-trifluoroethane, from about 1.9 to about 2.8 weight percent of ethanol, from about 7.7 to about 10.3 weight percent of acetone, from about 0.05 to about 0.2 weight percent of nitromethane and from about 0.3 to about 8.3 weight percent of hexane. The most preferred embodiment of the invention comprises from about 84.0 to about 86.3 weight percent of 1,1,2-trichloro-1,2,2-trifluoroethane, from about 2.1 to about 2.4 weight percent of ethanol, from about 7.8 to about 8.8 weight percent of acetone, from about 3.1 to about 5.9 weight percent of hexane, and from about 0.1 to about 0.2 weight percent of nitromethane. Such compositions possess constant or essentially constant boiling points of about 44.0° C. at 760 mm Hg. All compositions within the indicated ranges, as well as certain compositions outside the indicated ranges, are azeotrope-like, as defined more particularly below.

It has been found that these azeotrope-like compositions are stable, safe to use and that the preferred compositions of the invention are nonflammable (exhibit no flash point when tested by the Tag Open Cup test method—ASTM D1 310-16) and exhibit excellent solvency power. These compositions have been found to be particularly effective when employed in conventional degreasing units for the dissolution of lubricating and machine cutting oils and the cleaning of such oils from solid surfaces.

For the purpose of this discussion, by azeotrope-like composition is intended to mean that the composition behaves like a true azeotrope in terms of its constant boiling characteristics or tendency not to fractionate upon boiling or evaporation. Such composition may or may not be a true azeotrope. Thus, in such compositions, the composition of the vapor formed during boiling or evaporation is identical or substantially identical to the original liquid composition. Hence, during boiling or evaporation, the liquid composition, if it changes at all, changes only to a minimal or negligible extent. This is to be contrasted to non-azeotrope-like compositions in which during boiling or evaporation, the liquid composition changes to a substantial degree.

As is well known in this art, another characteristic of azeotrope-like compositions is that there is a range of compositions containing the same components in varying proportions which are azeotrope-like. All such compositions are intended to be covered by the term azeotrope-like as used herein. As an example, it is well known that at differing pressures, the composition of a given azeotrope will vary at least slightly and changes in distillation pressures also change, at least slightly, the distillation temperatures. Thus, an azeotrope of A and B represents a unique type of relationship but with a variable composition depending on temperature and/or pressure.

The 1,1,2-trichloro-1,2,2-trifluoroethane, ethanol, nitromethane, acetone and hexane components of the novel solvent azeotrope-like compositions of the invention are all commercially available. Preferably they should be used in sufficiently high purity so as to avoid the introduction of adverse influences upon the solvency properties or constant boiling properties of the system.

A suitable grade of 1,1,2-trichloro-1,2,2-trifluoroethane, for example, is sold by Allied Corporation under the trade name "GENESOLV ® D".

The term "hexane" is used herein as to mean any $C_6$ paraffin hydrocarbon ($C_6H_{14}$) (see Hackh's Chemical Dictionary, 3rd Ed., McGraw Hill Book Co. (1944) p. 408). Thus, the term "hexane" includes n-hexane, 2-methylpentane, 3-methylpentane, 2,2-dimethylbutane, 2,3-dimethylbutane and any and all mixtures thereof. Specifically included is commercial "isohexane" which typically contains from about 35 to about 100 weight percent of 2-methylpentane admixed with other hexane isomers. It has been found that each hexane isomer, separately and in combination with other hexane isomers, form azeotrope-like compositions with 1,1,2-trichloro-1,2,2-trifluoroethane, ethanol, acetone and nitromethane in accordance with the invention.

EXAMPLES 1–9

The azeotrope-like compositions of the invention were determined through the use of distillation techniques designed to provide higher rectification of the distillate than found in the most demanding vapor degreaser systems. For this purpose a five theoretical plate Oldershaw distillation column was used with a cold water condensed, manual liquid dividing head. Typically, approximately 350 cc of liquid were charged to the distillation pot. The liquid was a mixture comprised of various combinations of 1,1,2-trichloro-1,2,2-trifluoroethane, acetone, ethanol, nitromethane and hexane.

The mixture was heated at total reflux for about one hour to ensure equilibration. For most of the runs, the distillate was obtained using a 2:1 reflux ratio at a boil-up rate of 400–500 grams per hr. Approximately 300 cc of product were distilled and 6 approximately equivalent sized overhead cuts were collected. The vapor temperature (of the distillate), pot temperature, and barometric pressure were monitored, A constant boiling fraction was collected and analyzed by gas chromatography to determine the weight percentages of its components. To normalize observed boiling points during different days to 760 mm of mercury pressure, the approximate normal boiling points of 1,1,2-trichloro-1,2,2-trifluoroethane rich mixtures were estimated by applying a barometric correction factor of about 26 mm Hg/°C., to the observed values. However, it is to be noted that this corrected boiling point is generally accurate up to ±0.4° C. and serves only as a rough comparison of boiling points determined on different days. By the above-described method, it was discovered that a constant boiling mixture boiling at 44.0±0.2° C. at 760 mm Hg was formed for compositions comprising 79.6 to 89.9 weight percent 1,1,2-trichloro-1,2,2-trifluoroethane, 1.9 to 2.3 weight percent ethanol, 7.7 to 10.3 weight percent acetone, 0.05 to 0.1 weight percent nitromethane, and 0.4 to 8.0 weight percent 2-methylpentane (2-MP). Supporting distillation data for the mixtures studied are shown in Table I.

TABLE I

| Example (Distillation) | FC-113 | EtOH | Acetone | Nitromethane | 2-MP |
|---|---|---|---|---|---|
| Starting Material (wt %) | | | | | |
| 1 | 67.4 | 8.2 | 16.6 | 0.8 | 7.0 |
| 2 | 76.3 | 3.0 | 11.0 | 0.5 | 9.2 |
| 3 | 77.7 | 3.1 | 11.0 | 0.2 | 8.0 |
| 4 | 79.9 | 2.2 | 10.2 | 0.1 | 7.6 |
| 5 | 84.7 | 1.0 | 6.1 | 0.2 | 8.0 |
| 6 | 81.5 | 3.0 | 11.0 | 0.5 | 4.0 |
| 7 | 85.0 | 3.0 | 10.9 | 0.1 | 1.0 |
| 8 | 91.9 | 1.0 | 5.9 | 0.2 | 1.0 |
| 9 | 92.3 | 1.0 | 6.1 | 0.2 | 0.4 |
| Constant Boiling Distillation Fraction (wt %) | | | | | |
| 1 | 79.6 | 2.3 | 10.3 | 0.1 | 7.7 |
| 2 | 79.6 | 2.3 | 10.0 | 0.1 | 8.0 |
| 3 | 80.6 | 2.2 | 10.1 | <0.1 | 7.0 |
| 4 | 81.4 | 2.0 | 10.0 | 0.1 | 6.5 |
| 5 | 83.1 | 2.0 | 8.8 | 0.1 | 6.0 |
| 6 | 84.7 | 2.1 | 9.2 | 0.1 | 3.9 |
| 7 | 87.9 | 2.0 | 8.9 | <0.1 | 1.1 |
| 8 | 89.3 | 1.9 | 7.7 | 0.1 | 1.0 |
| 9 | 89.9 | 1.9 | 7.7 | <0.1 | 0.4 |

| | Vapor Temp (°C.) | Barometric Pressure (mm Hg) | Approx. B.P. Corrected to 760 mm | |
|---|---|---|---|---|
| 1 | 43.3 | 744.9 | 43.9 | |
| 2 | 43.5 | 747.3 | 44.0 | |
| 3 | 43.2 | 731.1 | 44.2 | |
| 4 | 43.9 | 752.9 | 44.2 | |
| 5 | 43.7 | 747.7 | 44.2 | |
| 6 | 43.6 | 747.3 | 44.1 | |
| 7 | 43.4 | 747.7 | 43.9 | |
| 8 | 44.0 | 762.3 | 43.9 | |
| 9 | 43.2 | 745.7 | 43.8 | |
| | | | Average | 44.0° C. ± 0.2° C. |

From the above examples, it is readily apparent that additional constant boiling or essentially constant boiling mixtures of the same components can readily be identified by anyone of ordinary skill in this art by the method described. No attempt was made to fully characterize and define the true azeotrope in the system comprising 1,1,2-trichloro-1,2,2-trifluoroethane, ethanol, acetone, nitromethane and hexane, nor the outer limits of its compositional ranges which are constant boiling or essentially constant boiling. As indicated, anyone of ordinary skill in the art can readily ascertain other constant boiling or essentially constant boiling mixtures, it being kept in mind that "constant boiling" or "essentially constant boiling" for the purposes of this invention means constant boiling or essentially constant boiling in the environment of a vapor degreaser system such as utilized in the art. All such mixtures in accordance with the invention which are constant boiling or essentially constant boiling are "azeotrope-like" within the meaning of this invention.

EXAMPLES 10-13

The following examples demonstrate that each hexane isomer exhibits its own unique compositional identity in azeotrope-like mixtures with 1,1,2-trichloro-1,2,2-trifluoroethane, ethanol, acetone, and nitromethane and that each hexane isomer and mixtures thereof form azeotrope-like constant boiling mixtures at about 44.0±0.2° C. with such components. This was particularly surprising in view of the significant variation in boiling point among the various hexane isomers. The hexane isomers and their boiling points are shown in the following Table II.

TABLE II

| Hexane Isomer | Normal Boiling Point |
|---|---|
| 2,2-dimethylbutane | 49.75 |
| 2,3-dimethylbutane | 58.1 |
| 2-methylpentane (isohexane) | 60.13 |
| 3-methylpentane | 64 |
| n-hexane | 68.74 |

A number of distillations were performed utilizing a distillation apparatus and procedure as previously described in Examples 1-9. Isomeric ratios and concentrations of the other mixture components were varied in the distillation starting material. Isomer mixtures were used either in their proportions found in inexpensive commercial grade material or were synthesized by blending isomers in various proportions. Commercial grade isohexane as sold by Phillips Petroleum Company (46% isohexane) was analyzed by gas chromotography and found to typically contain:

| | wt % |
|---|---|
| 2-methylpentane | 46.5 |
| 3-methylpentane | 23.5 |
| 2,3-dimethylbutane | 14.4 |
| 2,2-dimethylbutane | 13.5 |
| n-hexane | 0.9 |
| isopentane | 0.2 |
| n-pentane | 0.1 |
| Unknown lights | 0.9 |

Distillation overhead fractions were collected and analyzed by gas chromatography. Constant boiling mixtures exhibiting a boiling point of approximately 44.0±0.5° C. were found to be formed comprising about 77.4 to 91.3 weight percent 1,1,2-trichloro-1,2,2-trifluoroethane, about 1.9 to 2.8 weight percent ethanol, about 7.6 to 11.3 weight percent acetone, about 0.1 to 0.4 weight percent nitromethane and about 0.3 to 8.2 weight percent hexane. The results are shown in following Table III. The results from Examples 1-9 are included. The results show that the mixtures studied are constant boiling or essentially constant boiling in the same context as described in connection with Example 1-9.

TABLE III

| | | Starting Material Compositions (wt %) | | | | |
|---|---|---|---|---|---|---|
| Examples | | FC-113 | Ethanol | Acetone | Nitromethane | 2,2-Dimethylbutane |
| 1-9 | | 67.4–92.3 | 1.0–8.2 | 5.9–16.6 | 0.1–0.8 | |
| 10 | (a) | 79.4 | 4.0 | 11.9 | 1.0 | |
| | (b) | 88.8 | 2.0 | 7.9 | 0.1 | |
| | (c) | 89.4 | 2.2 | 7.8 | 0.1 | |
| 11 | (a) | 83.9 | 2.4 | 8.1 | 0.3 | |
| | (b) | 84.4 | 2.1 | 7.0 | 0.5 | |
| 12 | | 78.7 | 2.5 | 9.5 | 0.2 | 1.0 |
| 13 | (a) | 80.3 | 2.0 | 10.1 | 0.3 | 0.9 |
| | (b) | 80.0 | 2.2 | 10.1 | 0.1 | 1.0 |
| | (c) | 80.0 | 2.2 | 10.1 | 0.1 | 1.0 |

| | 2,3-Dimethyl- | 2-Methyl | 3-Methyl | | Total |

TABLE III-continued

| Examples 1-9 | | butane | Pentane | Pentane | N—hexane | Hexane |
|---|---|---|---|---|---|---|
| 1-9 | | | 0.4-9.2 | | | 0.4-9.2 |
| 10 | (a) | | | | 3.0 | 3.0 |
|  | (b) | | | | 1.2 | 1.2 |
|  | (c) | | | | 0.5 | 0.5 |
| 11 | (a) | 2.7 | 2.6 | | | 5.3 |
|  | (b) | 3.0 | 3.0 | | | 6.0 |
| 12 | | 4.0 | 4.0 | | | 9.0 |
| 13 | (a) | 0.9 | 3.1 | 1.6 | 0.8 | 7.3 |
|  | (b) | 1.1 | 3.6 | 1.8 | 0.1 | 7.6 |
|  | (c) | 1.1 | 3.6 | 1.8 | 0.1 | 7.6 |

Constant Boiling Distillation Fraction (wt %)

| Examples | | FC-113 | Ethanol | Acetone | Nitro-methane | 2,2-Dimethyl-butane |
|---|---|---|---|---|---|---|
| 1-9 | | 79.6-89.9 | 1.9-2.3 | 7.7-10.3 | 0.05-0.1 | |
| 10 | (a) | 87.1 | 2.1 | 8.8 | 0.1 | |
|  | (b) | 89.1 | 2.1 | 8.0 | 0.1 | |
|  | (c) | 89.6 | 2.1 | 7.8 | <0.1 | |
| 11 | (a) | 84.1 | 2.3 | 8.5 | 0.1 | |
|  | (b) | 84.4 | 2.3 | 8.0 | 0.1 | |
| 12 | | 79.6 | 2.1 | 9.9 | <0.1 | 1.6 |
| 13 | (a) | 81.4 | 1.9 | 10.1 | 0.1 | 1.3 |
|  | (b) | 80.5 | 2.1 | 9.9 | 0.1 | 1.1 |
|  | (c) | 81.1 | 2.1 | 9.8 | 0.1 | 1.4 |

| Examples | | 2,3-Di-methyl-butane | 2-Methyl-Pentane | 3-Methyl-Pen-tane | N—hex-ane | To-tal Hex-ane | BP corr. to 760 mm (°C.) |
|---|---|---|---|---|---|---|---|
| 1-9 | | | 0.4-8.0 | | | 0.4-8.0 | 44.0 |
| 10 | (a) | | | | 1.6 | 1.6 | 43.9 |
|  | (b) | | | | 0.6 | 0.6 | 44.0 |
|  | (c) | | | | 0.3 | 0.3 | 44.0 |
| 11 | (a) | 2.7 | 2.3 | | | 5.0 | 43.8 |
|  | (b) | 2.6 | 2.7 | | | 5.2 | 43.9 |
| 12 | | 3.6 | 3.1 | | | 8.3 | 43.5 |
| 13 | (a) | 0.9 | 2.6 | 1.3 | 0.4 | 6.5 | 43.9 |
|  | (b) | 1.1 | 4.9 | | 0.1 | 7.2 | 44.0 |
|  | (c) | 1.1 | 4.5 | | <0.1 | 7.1 | 43.8 |

EXAMPLE 14

To illustrate the azeotrope-like nature of the mixtures of the invention under conditions of actual use in a vapor phase degreasing operation, a vapor phase degreasing machine was charged with a preferred azeotrope-like mixture in accordance with the invention comprising about 84.1 weight percent 1,1,2-trichloro-1,2,2-trifluoroethane (FC-113), about 2.3 weight percent ethanol, about 8.0 weight percent acetone, about 5.5 weight percent commercial grade isohexane and about 0.1 weight percent nitromethane. The mixture was evaluated for its constant boiling or non-segregating characteristics. Solvents were tested in either a Crest 3 sump VPD (Model No. 23033-01) or a Baron Blakeslee refrigeration cooled 3 sump VPD (Series 5000 machine—Model No. MLR-216). The solvent charge was brought to reflux and the individual sump compositions were determined with a Hewlett Packard 5890 Gas Chromatograph. Refluxing was continued for 48 hrs and sump compositions were monitored throughout this time. A mixture was considered constant boiling or non-segregating if the maximum concentration difference between sumps for any mixture component was less than 0.3%.

If the mixture were not azeotrope-like, the high boiling components would very quickly concentrate in the boil sump and be depleted in the rinse sump. As the data in Table IV show, this did not happen. These results indicate that the compositions of this invention will not segregate in a commercial vapor degreaser, thereby avoiding potential safety, performance, and handling problems. The preferred composition tested was also found to not have a flash point according to recommended procedures ASTM D-56 (Tag Closed Cup) and ASTM D-1310 (Tag open Cup).

TABLE IV

COMPOSITION, % WEIGHT

Sample Time, Boil Sump

| | 0 hr | 3 hr | 27 hr | 49 hr |
|---|---|---|---|---|
| FC-113 | 84.04 | 83.81 | 83.93 | 83.93 |
| Acetone | 8.04 | 7.89 | 7.81 | 7.79 |
| Ethanol | 2.32 | 2.50 | 2.47 | 2.45 |
| Total Hexane | 5.48 | 5.57 | 5.59 | 5.63 |
| Nitromethane | 0.13 | 0.23 | 0.20 | 0.20 |

Sample Time, Work Sump

| | 0 hr$^a$ | 3 hr | 27 hr | 49 hr |
|---|---|---|---|---|
| FC-113 | 84.04 | 83.95 | 84.28 | 84.24 |
| Acetone | 8.03 | 8.07 | 7.98 | 7.98 |
| Ethanol | 2.32 | 2.48 | 2.32 | 2.35 |
| Total Hexane | 5.48 | 5.36 | 5.33 | 5.33 |
| Nitromethane | 0.13 | 0.14 | 0.09 | 0.10 |

Sample Time, Rinse Sump

| | 0 hr$^a$ | 3 hr | 27 hr | 49 hr |
|---|---|---|---|---|
| FC-113 | 84.04 | 84.11 | 84.56 | 84.23 |
| Acetone | 8.03 | 8.10 | 8.06 | 8.01 |
| Ethanol | 2.32 | 2.39 | 2.27 | 2.37 |
| Total Hexane | 5.48 | 5.30 | 5.02 | 5.31 |
| Nitromethane | 0.13 | 0.10 | 0.09 | 0.08 |

$^a$Analytical Standard - representative of initial composition of all three sumps
$^b$Commercial Isohexane

EXAMPLE 15

This example illustrates the use of the preferred azeotrope-like composition of the invention to clean metal parts.

Cleaning was performed in a Branson B-400 two-sump vapor degreaser. A first sump was used as the working sump and held boiling solvent comprising about 84.1 weight percent 1,1,2-trichloro-1,2,2-trifluoroethane, about 2.3 weight percent ethanol, about 8.0 weight percent acetone, about 5.5 weight percent commercial grade isohexane and about 0.1 weight percent nitromethane. A second sump was used as the rinse sump. Refrigerated cooling coils lined the upper inner wall of the apparatus to maintain a vapor blanket. Soils were coated on two kinds of ¾"×3" metal coupons. These were 316 stainless steel and 2024 aluminum. Soils were selected from two classes of metal working fluids as follows:

| Name | Manufacturer | Class |
|---|---|---|
| Trimsol | Master Chem. Co. | Emulsifiable |
| 951 | Van Straaten Chem. Co. | Synthetic |

The metal coupons were sanded to give a totally clean, freshly exposed surface. Following a deionized water rinse, the coupons were rinsed in acetone followed by methanol and air dried for 10 minutes. Four identical coupons were then dipped into each of the metal working fluids. Cleaning tests were run on two of these coupons shortly after dipping into the metal working fluids. The other two coupons were tested after standing for 24 hours. For cleaning, the parts were placed on racks in a stainless steel wire mesh basket. In a first step, this assembly was immersed in the work sump for two minutes, then transferred to the rinse sump for two minutes, followed by a two minute solvent distillate spray in the vapor zone. The final step was a one minute hold in the vapor zone.

The treated coupons were visually inspected for evidence of soil residue. A water-break test was also applied wherein the coupons were immersed in water and allowed to drain for 10 seconds. The coupon surface was examined for breaks in the water film over the 10 second draining period. A coupon was considered totally clean if no soil residues or breaks in the water film during the water break test were noticeable on the surface of the coupon. In the above-described manner, "316" stainless steel coupons were soiled with Trimsol metal working fluid and with 951 metal working fluid, and "2024" aluminum coupons were soiled with Trimsol metal working fluid. All these soiled coupons were cleaned with the preferred azeotrope-like compositions of the invention and evaluated for cleanliness as described above. All the coupons were judged to be totally clean.

We claim:

1. Azeotrope-like compositions comprising trichlorotrifluoroethane, ethanol, nitromethane, acetone and hexane.

2. Azeotrope-like compositions according to claim 1 wherein said trichlorotrifluoroethane is 1,1,2-trichloro-1,2,2-trifluoroethane.

3. Azeotrope-like compositions according to claim 2 wherein said hexane is n-hexane.

4. Azeotrope-like compositions according to claim 2 wherein said hexane is 2-methylpentane.

5. Azeotrope-like compositions according to claim 2 wherein said hexane is 3-methylpentane.

6. Azeotrope-like compositions according to claim 2 wherein said hexane is 2,2-dimethylbutane.

7. Azeotrope-like compositions according to claim 2 wherein said hexane is 2,3-dimethylbutane.

8. Azeotrope-like compositions according to claim 2 wherein said hexane is isohexane.

9. Azeotrope-like compositions according to claim 2 comprising from about 67.6 to about 90.5 weight percent 1,1,2-trichloro-1,2,2-trifluoroethane, from about 1.5 to about 8.1 weight percent ethanol, from 7.4 to about 16.6 weight percent acetone, from about 0.05 to about 0.5 weight percent nitromethane and from about 0.2 to about 8.3 weight percent hexane.

10. Azeotrope-like compositions according to claim 2 wherein said weight percent 1,1,2-trichloro-1,2,2-trifluoroethane is from about 79.6 to about 89.9, said weight percent ethanol is from about 1.9 to about 2.8, said weight percent acetone is from about 7.7 to about 10.3, said weight percent nitromethane is from about 0.05 to about 0.2 and said weight percent hexane is from about 0.3 to about 8.3.

11. Azeotrope-like compositions according to claim 2 wherein said weight percent of 1,1,2-trichloro-1,2,2-trifluoroethane is from about 84.0 to about 86.3, said weight percent ethanol is from about 2.1 to about 2.4, said weight percent acetone is from about 7.8 to about 8.8, said weight percent nitromethane is from about 0.1 to about 0.2, said weight percent hexane is from about 3.1 to about 5.9.

12. Azeotrope-like compositions according to claim 11 wherein said hexane is isohexane.

13. The method of cleaning a solid surface which comprises treating said surface with an azeotrope-like composition as defined in claim 1.

14. The method of cleaning a solid surface which comprises treating said surface with an azeotrope-like composition as defined in claim 2.

15. The method of cleaning a solid surface which comprises treating said surface with an azeotrope-like composition as defined in claim 8.

16. The method of cleaning a solid surface which comprises treating said surface with an azeotrope-like composition as defined in claim 11.

* * * * *